United States Patent

Beil

Patent Number: 6,146,354
Date of Patent: *Nov. 14, 2000

[54] ASYMMETRICAL MULTI-LUMEN APHERESIS CATHETER WITH BALANCED FLOW RATES

[75] Inventor: Craig M. Beil, Norristown, Pa.

[73] Assignee: Horizon Medical Products, Atlanta, Ga.

[*] Notice: This patent issued on a continued prosecution application filed under 37 CFR 1.53(d), and is subject to the twenty year patent term provisions of 35 U.S.C. 154(a)(2).

[21] Appl. No.: 08/653,447

[22] Filed: May 24, 1996

[51] Int. Cl.$^7$ ................................................ A61M 1/00
[52] U.S. Cl. ........................... 604/28; 604/4.01; 604/43; 604/523
[58] Field of Search ........................ 604/264, 280, 604/43, 4–6, 28, 523, 40.1

[56] References Cited

U.S. PATENT DOCUMENTS

| | | | |
|---|---|---|---|
| D. 272,651 | 2/1984 | Mahurkar | D24/54 |
| 4,134,402 | 1/1979 | Mahurkar | 128/214 R |
| 4,568,329 | 2/1986 | Mahurkar | 604/43 |
| 4,583,968 | 4/1986 | Mahurkar | 604/43 |
| 4,619,643 | 10/1986 | Bai | 604/43 |
| 4,643,711 | 2/1987 | Bates . | |
| 4,692,141 | 9/1987 | Mahurkar | 604/43 |
| 4,770,652 | 9/1988 | Mahurkar | 604/4 |
| 4,808,155 | 2/1989 | Mahurkar | 604/43 |
| 4,842,582 | 6/1989 | Mahurkar | 604/43 |
| 4,895,561 | 1/1990 | Mahurkar | 604/43 |
| 4,917,667 | 4/1990 | Jackson | 604/264 |
| 4,990,139 | 2/1991 | Jang | 604/101 |
| 5,221,256 | 6/1993 | Mahurkar | 604/43 |
| 5,342,301 | 8/1994 | Saab | 604/96 |
| 5,374,245 | 12/1994 | Mahurkar | 604/43 |
| 5,378,230 | 1/1995 | Mahurkar | 604/264 |
| 5,380,276 | 1/1995 | Miller et al. | 604/28 |
| 5,382,238 | 1/1995 | Abrahamson et al. | 604/170 |
| 5,451,206 | 9/1995 | Young | 604/43 |
| 5,476,453 | 12/1995 | Mehta | 604/281 |
| 5,556,390 | 9/1996 | Hicks | 604/264 |

FOREIGN PATENT DOCUMENTS

| | | |
|---|---|---|
| 1193508 | 9/1985 | Canada . |
| WO 95/04567 | 2/1995 | WIPO . |

Primary Examiner—Mark Bockelman
Attorney, Agent, or Firm—Woodcock Washburn Kurtz Mackiewicz & Norris LLP

[57] ABSTRACT

A multi-lumen intravenous catheter for use in treating a patient's blood comprising an elongated cylindrical tube with at least first, second and third lumens formed inside. The first lumen is adapted to accept a guide wire for guiding the catheter during insertion into a blood vessel of the patient or therapeutics for introduction into the patient's bloodstream. The second lumen is adapted to return treated blood to the patient's blood vessel and has a smooth, circular or ellipsoidal cross-section. The third lumen is adapted to extract blood from the patient's blood vessel for treatment and has a substantially elliptical or football-shaped cross-section and a cross-sectional area which is 10 to 30 percent larger than a cross-sectional area of the second lumen. Despite such unbalanced cross-sections, the second and third lumens have substantially equal blood flow rates during treatment of the patient's blood. Also, the intake and return flow rates are improved for a given cross-sectional area of the catheter while the hydrostatic pressures within the lumens stay within maximum acceptable hydrostatic pressure limits for the patient.

13 Claims, 4 Drawing Sheets

ASYMMETRICAL MULTI-LUMEN APHERESIS CATHETER WITH BALANCED FLOW RATES

FIELD OF THE INVENTION

The present invention relates generally to multiple lumen catheters for use in medical applications such as hemodialysis where fluids must flow simultaneously to and from a patient. More particularly, the present invention relates to a triple lumen critical care catheter which has two lumens used for hemodialysis and a third lumen for use in inserting medication, withdrawing blood samples for analysis, measuring hydrostatic pressures in the patient's blood vessels, and the like while hemodialysis is being performed. The invention specifically relates to a triple lumen critical care catheter with an arterial intake lumen which is substantially larger than the venous return lumen whereby the intake and return flow rates are improved for a given cross-sectional area of the catheter and the hydrostatic pressures within the lumens are within maximum acceptable hydrostatic pressure limits.

BACKGROUND OF THE INVENTION

Figure 1:
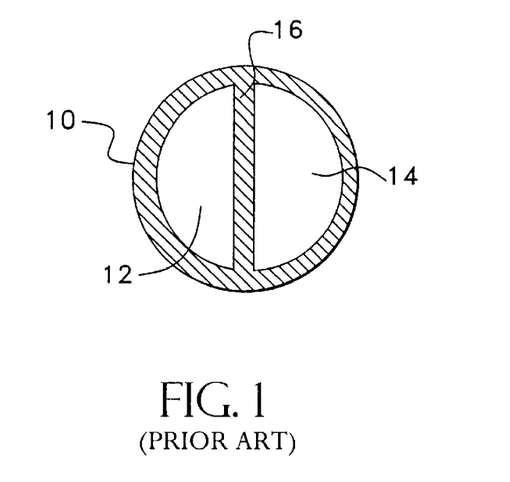
FIG. 1 is a cross-sectional view of a prior art "Double D" dual lumen catheter.

FIG. 1 illustrates the cross-section of the conventional "Double D" dual lumen catheter 10 of the type described in U.S. Pat. No. 4,134,402, Des. 272,651, U.S. Pat. Nos. 4,568,329, 4,692,141, 4,583,968, 4,770,652, 4,808,155, 4,842,582, 4,895,561, and Canadian Patent No. 1,193,508 by Dr. Sakharam Mahurkar for use during hemodialysis to prevent the need to insert separate catheters for extracting the patient's untreated blood and returning the treated blood to the patient. As known to those skilled in the art, the catheter 10 is inserted into a blood vessel (vein and/or artery) of the patient, and the patient's untreated blood is extracted through lumen 12 for extracorporeal blood purification by a hemodialysis device. The dialyzed blood is then returned to the patient's blood vessel via lumen 14. Septum 16 separates lumens 12 and 14 and divides the catheter 10 into two equal halves whereby the lumens hold substantially similar volumes of blood. Septum 16 further prevents the intermixing of the treated and untreated blood. During hemodialysis, such a geometry is purported to provide a bidirectional blood flow rate of 250 ml per minute with a pressure gradient under 100 mm Hg.

Figure 2:
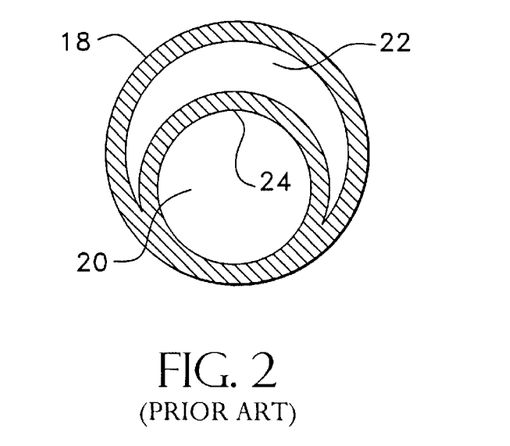
FIG. 2 is a cross-sectional view of a prior art "Circle C" dual lumen catheter.

FIG. 2 illustrates the cross-section of the conventional "Circle C" dual lumen catheter 18 of the type described, for example, in U.S. Pat. No. 5,380,276 to Miller et al. The catheter 18 disclosed by Miller et al. operates in a similar manner as that illustrated in FIG. 1 except for the cross-sectional configuration of the catheter. As shown in FIG. 2, the "venous" lumen 20 for returning the treated blood to the patient has a circular cross-section, while the "arterial" lumen 22 for removing the untreated blood from the patient has a crescent-shaped cross-section. Miller et al. specifically designed the catheter of FIG. 2 so that the cross-sectional area of venous lumen 20 is substantially equal to the cross-sectional area of arterial lumen 22 for each catheter french size. Circular septum 24 prevents the intermixing of the treated and untreated blood.

Figure 3:
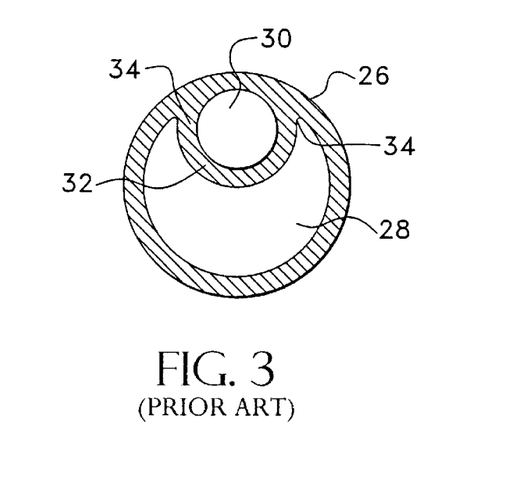
FIG. 3 is a cross-sectional view of a prior art "Circle C" dual lumen catheter modified to have unequal cross-sectional areas for the respective lumens.

Catheters with lumens having cross-sections with sharp corners as in FIGS. 1 and 2 have been found to cause platelet formation in the corners due to the reduced blood flows in the corners. Accordingly, the present assignee previously designed a modified "Circle C" dual lumen catheter 26 having all smooth transitions within the cross-sections of the arterial lumen 28 and the venous lumen 30 by using a septum 32 which was thickened in the corners 34 as illustrated in FIG. 3. Catheter 26 was also designed to have unequal cross-sectional areas for the respective lumens. In particular, the arterial intake lumen 28 was designed to have a cross-sectional area substantially larger than the cross-sectional area of the venous return lumen 30. Such a design was found to lower the intake vacuum and to raise the venous pressure to a substantially balanced level for each flow rate.

When treating "critical care" patients subject to renal failure, it is often desired to provide additional lumens besides the venous and arterial lumens in order to facilitate the insertion of a guide wire or therapeutic agents, to monitor hydrostatic pressure of the patient, and the like. Triple lumen catheters have been designed for this purpose. Unfortunately, not all provide cross-sections which permit flow rates sufficient for hemodialysis.

Figure 4:
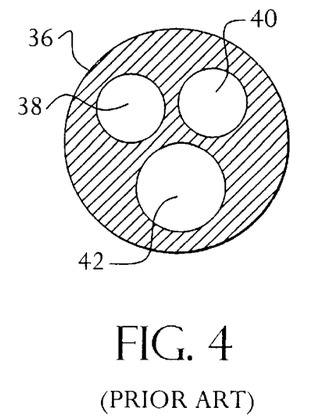
FIG. 4 is a cross-sectional view of a prior art low flow triple lumen catheter.

FIG. 4 is a cross-sectional view of a prior art low flow triple lumen critical care catheter 36 designed by the present assignee. In this design, three independent dedicated lumens 38, 40, and 42 are provided in a single catheter 36 for allowing the simultaneous and continuous monitoring and treatment of several parameters of seriously ill patients. However, because of the small size of the lumens relative to the outer diameter of catheter 36 and the resulting inefficient flow geometries, the design of FIG. 4 has not been found to be particularly suitable for critical care applications such as hemodialysis which require high flow rates on the order of 250 ml per minute.

Figure 5:
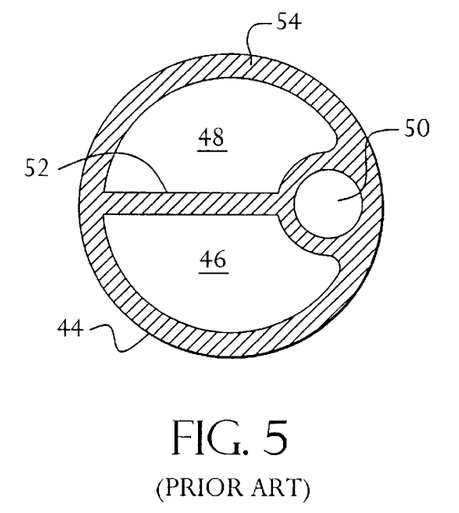
FIG. 5 is a cross-sectional view of a prior art triple lumen critical care catheter of the type disclosed by Mahurkar in U.S. Pat. No. 5,221,256.

Prior art triple lumen "critical care" catheters designed for higher flow rates are illustrated in FIGS. 5–9. For example, FIG. 5 is a cross-sectional view of a prior art triple lumen critical care catheter 44 of the type disclosed by Mahurkar in U.S. Pat. No. 5,221,256. As shown in FIG. 5, Mahurkar substantially maintained the "Double D" design for the venous lumen 46 and the arterial lumen 48 except that a small third lumen 50 for accepting a guide wire is located at the intersection of one diametral end of the septum 52 and the outer tube 54 between a pair of adjacent corners of the lumens 46 and 48. As in the "Double D" dual lumen configuration, the cross-sectional areas of the venous lumen 46 and the arterial lumen 48 are kept balanced.

Figure 6:
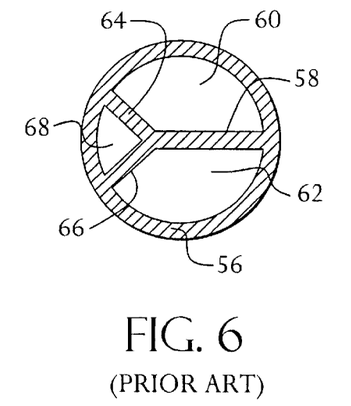
FIG. 6 is a cross-sectional view of a prior art triple lumen critical care catheter of the type disclosed by Young in U.S. Pat. No. 5,451,206 to maximize the total cross-sectional area of the combined lumens.

FIG. 6 is a cross-sectional view of a prior art triple lumen critical care catheter 56 of the type disclosed by Young in U.S. Pat. No. 5,451,206 for maximizing the total cross-sectional area of the combined lumens. In particular, catheter 56 includes a major septum 58 which divides the catheter generally into venous lumen 60 and arterial lumen 62. However, septum 58 bifurcates into a pair of generally flat minor septums 64 and 66 to form a triangular-shaped third lumen 68 located between the adjacent corners of the generally D-shaped lumens 60 and 62. As in the triple lumen catheter illustrated in FIG. 5, the venous lumen 60 and arterial lumen 62 of catheter 56 of FIG. 6 have substantially the same cross-sectional areas and sufficient size to support flow rates of at least 250 ml per minute. However, as noted above, catheters with lumens having cross-sections with such sharp corners have been found to cause platelet formation in the corners due to the reduced blood flows in the corners and are not particularly desirable for hemodialysis applications.

Figure 7:
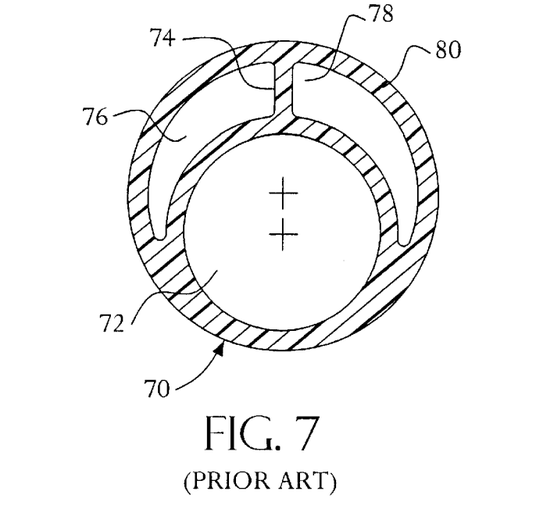
FIG. 7 is a cross-sectional view of a prior art triple lumen catheter of the type disclosed by Mahurkar in U.S. Pat. No. 5,378,230, where the large lumen is circular in cross-section.
Figure 8:
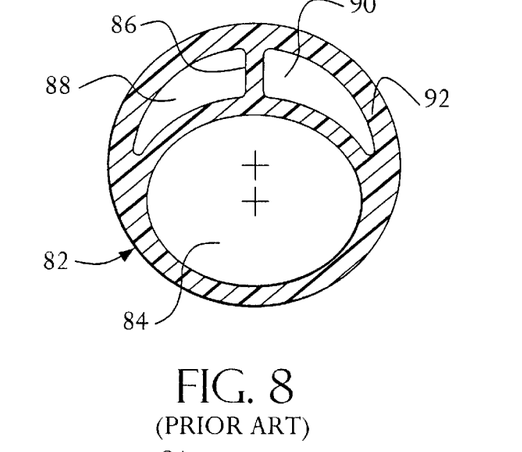
FIG. 8 is a cross-sectional view of a prior art triple lumen catheter of the type disclosed by Mahurkar in U.S. Pat. No. 5,378,230, where the large lumen is elliptical in cross-section.

FIGS. 7 and 8 illustrate triple lumen versions of the "Circle C" design described above with respect to FIG. 2 but tailored to the needs of patients suffering from shock, trauma, dehydration, or chemical or infectious circulatory collapse. In particular, FIGS. 7 and 8 are cross-sectional views of prior art triple lumen critical care catheters of the type disclosed by Mahurkar in U.S. Pat. No. 5,378,230. In FIG. 7, the large lumen 72 of catheter 70 is circular in cross-section and is used to infuse large volumes of liquid into the patient at a high rate, as when fluids are infused from an I.V. fluid source hung from a height of three to four feet. In other words, large lumen 72 functions as a venous lumen for infusing fluids into the patient. Septum 74 separates the crescent shaped lumen into second and third lumens 76 and 78 bounded by the outer diameter 80 of the catheter 70 for injections of medications, for taking blood samples, or for monitoring the hydrostatic pressure in the blood vessels of the patient. FIG. 8 illustrates a closely related embodiment of a catheter 82 in which the large venous lumen 84 is elliptical in cross-section and the septum 86 separates the crescent shaped lumen into relatively smaller second and third lumens 88 and 90 bounded by the outer diameter 92 of the catheter 82. As in the embodiment of FIG. 7, lumens 88 and 90 are used to inject medications, to take blood samples, or to monitor the hydrostatic pressure in the blood vessels of the patient. Mahurkar does not suggest in U.S. Pat. No. 5,378,230 that such "unbalanced" catheters may be used for hemodialysis applications.

Figure 9:
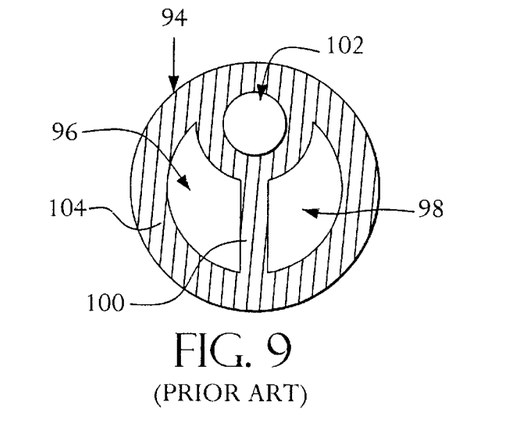
FIG. 9 is a cross-sectional view of a prior art "longhorn" triple lumen critical care catheter.

FIG. 9 is a cross-sectional view of a prior art "longhorn" triple lumen critical care catheter 94 previously designed by the present assignee to provide flow rates suitable for hemodialysis. The "longhorn" triple lumen design includes venous lumen 96 and arterial lumen 98 separated by a planar septum 100. The third lumen 102 is located at the intersection of one diametral end of the septum 100 and the outer tube 104 between a pair of adjacent corners of the lumens 96 and 98. As in the configuration of FIG. 5, the cross-sectional areas of the venous lumen 96 and the arterial lumen 98 are kept balanced. A triple lumen critical care catheter which supports flow rates suitable for hemodialysis applications and performs as well or better than the designs of prior art FIGS. 5 and 9 is desired. As will be explained in more detail below, the present inventor has discovered that improved flow rates could be achieved by providing "unbalanced" smooth arterial and venous lumens with smooth contours. Substantial improvements in flow rates and pressures for a given french size were discovered for the particular configurations described below.

SUMMARY OF THE INVENTION

The present invention relates to a multi-lumen critical care catheter and associated system and method for use in treating a patient's body fluid such as blood. The critical care apheresis catheter of the invention is particularly designed to support the flow rates necessary for hemodialysis while also providing a separate lumen for accepting a guide wire, introducing therapeutics, taking blood samples, and the like. In a preferred embodiment of the invention, the catheter comprises an elongated cylindrical tube with at least first, second and third lumens formed therein, where the first lumen is adapted to accept a guide wire for guiding the catheter during insertion into a blood vessel of the patient or therapeutics for introduction into the patient's bloodstream, the second lumen is adapted to return treated blood to the patient's blood vessel and has a smooth cross-section, and the third lumen is adapted to extract blood from the patient's blood vessel for treatment and has a substantially ellipsoidal cross-section and a cross-sectional area which is at least 10 percent larger than a cross-sectional area of the second lumen. In accordance with the invention, despite such unbalanced cross-sections, the second and third lumens have substantially equal blood flow rates during treatment of the patient's blood.

Preferably, the third lumen has tapered ends at respective ends along a major axis of the ellipsoidal cross-section of the third lumen so as to form a substantially football-shaped cross-section. On the other hand, the third lumen may have an elliptical cross-section. Preferably, the third lumen has a cross-sectional area which is 10 to 30 percent larger than the cross-sectional area of the second lumen. In a presently preferred commercial embodiment, the third lumen has a cross-sectional area which is approximately 25 percent larger than a cross-sectional area of the second lumen. The second lumen may be circular or ellipsoidal in cross-section.

A triple lumen catheter so designed has been found to have improved intake and return flow rates for a given cross-sectional area of the catheter while the hydrostatic pressures within the lumens stay within maximum acceptable hydrostatic pressure limits for the patient. Also, since the catheter lumens have smooth profiles, slow moving currents within the lumen are avoided, thereby minimizing the likelihood of platelet formation. Further beneficial features of the invention will become apparent to those skilled in the art from the following detailed description of the invention.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PREFERRED EMBODIMENT

A system and method which provides flow rates suitable for hemodialysis applications and provides other beneficial features in accordance with the presently preferred exemplary embodiment of the invention will be described below with reference to FIGS. 10–12. Those skilled in the art will readily appreciate that the description given herein with respect to those figures is for explanatory purposes only and is not intended in any way to limit the scope of the invention. All questions regarding the scope of the invention should be resolved by referring to the appended claims.

Figure 10:
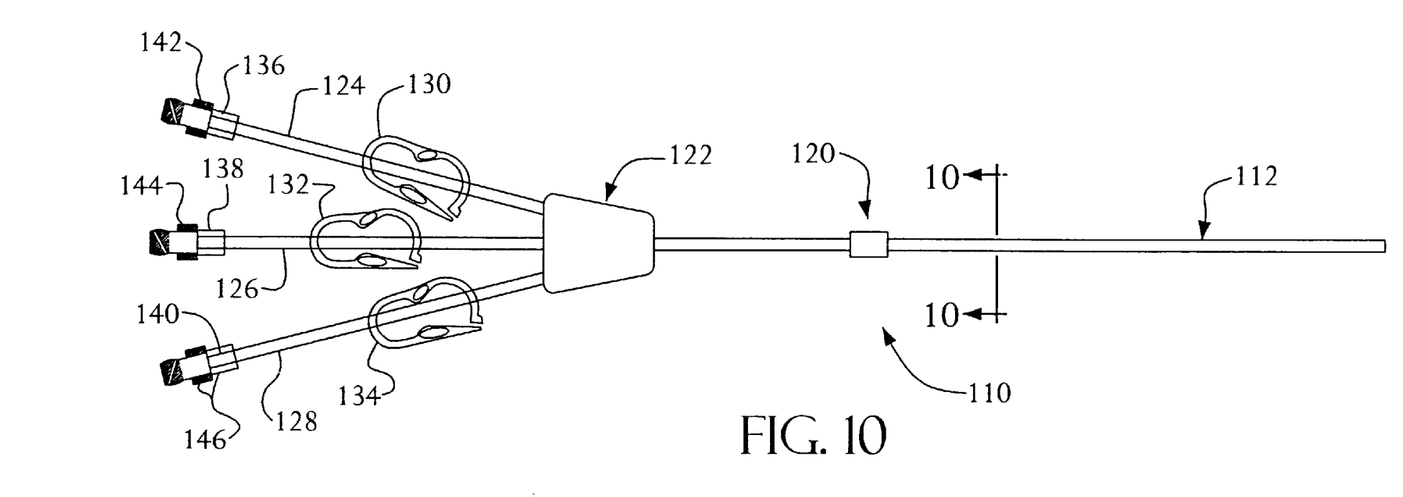
FIG. 10 is a perspective view of a triple lumen critical care catheter embodying the present invention.
Figure 11:
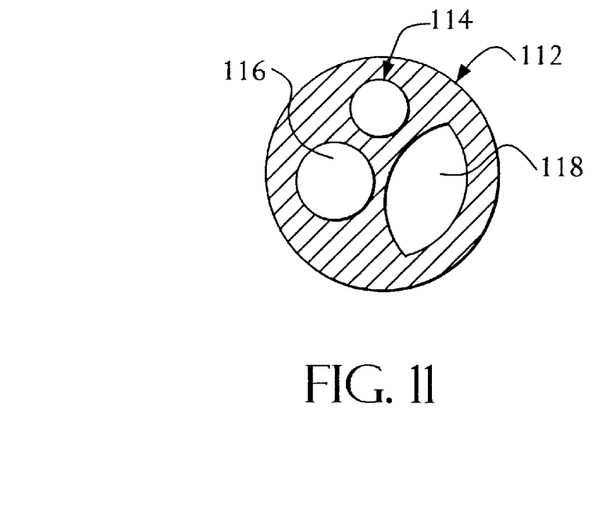
FIG. 11 is a cross-sectional view of a triple lumen critical care catheter in accordance with a first embodiment of the invention.
Figure 12:
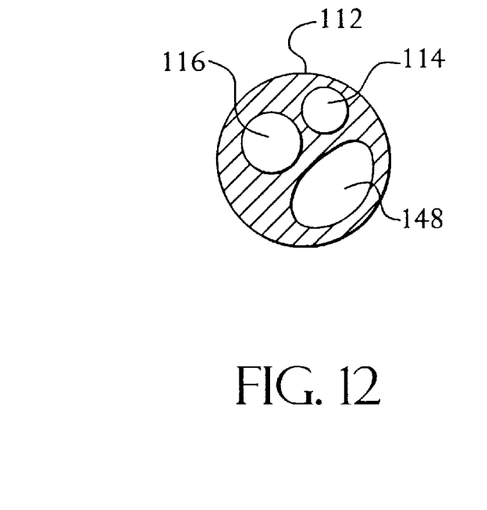
FIG. 12 is a cross-sectional view of a triple lumen critical care catheter in accordance with a second embodiment of the invention.

FIGS. 10–12 illustrate a triple lumen critical care catheter 110 in accordance with the invention. Catheter 110 has an elongated cylindrical body portion 112 preferably made of silicone, although cylindrical body portion 112 may alternatively be made of polyurethane or cross-linked polyethylene if so desired. The tubular body portion 112 contains three parallel lumens 114, 116, and 118, as will be described in more detail below with respect to FIGS. 11 and 12. A polyester cuff 120 is adhered to the silicon tube 112 using a medical adhesive. Polyester cuff 120 secures the catheter to the patient's skin in a known manner to prevent the opening in the patient's skin from weeping during use of the catheter 110.

In a presently preferred embodiment of catheter 110, the catheter is provided with a blunt tip. Thus, prior to hemodialysis use, the catheter 110 is cut to length, and the arterial lumen is cut back approximately 1 inch from the end using a razor blade or other sharp instrument so that the blood intake in the exposed arterial lumen will occur approximately 1 inch upstream from the point where the venous lumen returns the treated blood into the patient's blood vessel. This is desired to prevent the mixing of the treated and untreated blood. Of course, other types of tips may be used as well, such as the conical tips described in the afore-mentioned Mahurkar patents.

At the proximal end of the catheter 110, the three lumens 114, 116, and 118 open up into a Y-shaped connector or hub 122 which forms three internal, separate passageways which communicate with the proximal ends of the lumens 114, 116, and 118. The proximal ends of the catheter lumens 114, 116, and 118 are generally expanded slightly to fit over mating sections at the distal end of the hub 122, and the inside walls of the catheter lumens 114, 116, and 118 are bonded to the mating walls of the hub 122 by conventional techniques such as vulcanization or thermal plastic welding. Alternatively, the hub 122 may be molded in place on the end of the catheter 110 using mold inserts to form the passageways of the hub 122. The hub passageways 122 diverge from each other as they extend towards the proximal end of the hub 122 and also increase in cross-sectional area.

To facilitate connection of the catheter hub 122 to the conventional tubes leading to a dialysis unit, injection syringes, or other extracorporeal equipment, extension tubes 124, 126, and 128 extend from the proximal end of the hub 122. Clamps 130, 132, and 134 are also placed on the extension tubes 124, 126, and 128, respectively, to permit opening and closing of the respective fluid passageways, thereby controlling the flow of blood between the catheter 110 and the dialysis unit (not shown). Extension tubes 124, 126, and 128 are soft and flexible and are easily manipulated and easily closed by the pressure of the clamps 130, 132, and 134. The proximal ends of the extension tubes 124, 126, and 128 receive respective ferrules 136, 138, and 140 formed as integral parts of female luer connectors 142, 144, and 146. The luer connectors 142, 144, and 146 couple the proximal ends of the respective extension tubes 124, 126, and 128 to the flexible tubes leading to the extracorporeal equipment (not shown). Of course, extension tubes 124, 126, and 128 may also be U-shaped in order to reduce the risk of accidental dislodgement of the catheter 110 from the patient during hemodialysis.

FIG. 11 illustrates the cross-sectional view along line 10—10 of FIG. 10 in accordance with a first embodiment of the invention. As shown, a relatively small lumen 114 with a circular cross-section is provided for accepting a guide wire, for injecting therapeutics into the patient's bloodstream, for withdrawing blood samples from the patient, for measuring the pressure in the blood vessel of the patient, and the like. A venous return lumen 116 with a substantially circular cross-section provides a venous return path for returning the treated blood to the patient. A circular cross-section is generally preferred since it is smooth in profile and thus provides the least flow disturbance and hence the best flow rates for the blood. Also, since the venous lumen 116 is smooth in profile, no slow moving currents form within the venous lumen 116 which may lead to the formation of platelets or blood clots.

An arterial intake lumen 118 with a substantially smooth ellipsoidal cross-section is provided for creating a vacuum pressure used to remove blood from the patient through capillary action. As shown in FIG. 11, the arterial lumen 118 may preferably have an ellipsoidal cross-section in the shape of a football, or, as shown in FIG. 12, the arterial lumen 148 may also have an ellipsoidal cross-section in the shape of an ellipse. As with the venous lumen 116, the arterial lumen 118 is smooth in profile to avoid slow moving currents within the arterial lumen 118 which may lead to the formation of platelets or blood clots. Also, in accordance with the invention, it is desired that the cross-sectional areas of the arterial intake lumens 118 or 148 be at least 10%. larger than the cross-sectional area of the venous return lumen 116 for a catheter 110 of a particular french size in order to better balance the flows within the respective lumens 116 and 118. In a presently preferred commercial embodiment, the arterial intake lumen 118 has a cross-sectional area which is approximately 25% greater than the cross-sectional area of the venous return lumen 116; however, optimum flow characteristics are also achievable if the arterial intake lumen 118 has a cross-sectional area which is anywhere from approximately 10% to approximately 30% greater than the cross-sectional area of the venous return lumen 116.

To provide a measure of the flow rates and resulting pressures in the arterial and venous lumens of a catheter having the cross-section illustrated in FIG. 11 with respect to the "longhorn" catheter with the cross-section illustrated in FIG. 9, the following test arrangement was created.

First, so that testing could be performed without human subjects, a test fluid with the same viscosity as blood was created (human blood has a viscosity of 3.5–4.0 Centipose). In particular, 1000 ml of water was mixed with 317.5 ml of glycerol to obtain a mixture of 40% by weight of glycerol. The resulting "Syn-Blood" had a viscosity of 3.646 Centipose.

The "Syn-Blood" was then run through a test stand using a 4509 Extracorporeal Module Pressure and Vacuum Unit and a 4533 Accessories Module Blood Pump and Flow Meter Unit made by Drake Willock. The test stand was set up by first attaching an appropriate blood line to the Extracorporeal Module. The pre-pump monitor line was then attached to the arterial vacuum gauge module, and the post pump monitor line was attached to the venous pressure gauge on the accessories module. The intake and return lines were then placed into a 1000 ml beaker half full of "Syn-Blood." The pump was run to fill the lines of the catheter and to displace all of the air bubbles. The arterial (intake) line on the pump was then attached to the arterial intake leg of the catheter. The venous (return) line on the pump was then attached to the venous (return) leg on the catheter. The pump was run again to displace any air bubbles. Then, with the catheter tip completely submerged in the Syn-Blood, the pump was run at 50 ml/min and the venous pressure and arterial vacuum were recorded. The flow rate of the pump was then increased to 100 ml/min and the venous pressure and arterial vacuum again were recorded. Since the pressure and vacuum pulsated slightly, the high values were recorded. This process was repeated for each flow rate until the venous pressure or arterial vacuum went off of the scale of the gauge (160 mm Hg vacuum; 310 mm Hg pressure). This process was repeated for each catheter.

Table 1 illustrates the flow rates determined using the experimental set-up for the catheter with the cross-section illustrated in FIG. 11 (the outer diameter of the catheter tested was, on average, 0.165 inch), while Table 2 illustrates the flow rates using the experimental set-up for the "longhorn" catheter with the cross-section illustrated in FIG. 9 and an average outer diameter of 0.164 inch for the actual catheter tested. In each case, a * means that the pressures were beyond the range of the measuring instrument. The cross-sectional area of the arterial lumen on the FIG. 11 catheter was 0.00425 square inch, while the cross-sectional area of the venous lumen on the FIG. 11 catheter was 0.00336 square inch, for a difference in cross-sectional area of 26 percent. The cross-sectional areas of the arterial and venous lumens of the FIG. 9 catheter were both approximately 0.00327 square inch. Both catheters could fit through a 13 french spreadable sheath with an inner diameter of 0.170 inch.

TABLE 1

TRIPLE LUMEN CATHETER FLOW DATA FOR FIG. 11 DESIGN

| Flow Rate mL/Min. | 50 | 100 | 150 | 200 | 250 | 300 |
|---|---|---|---|---|---|---|
| Arterial (VAC) mm Hg | 20 | 70 | 100 | 145 | 160 | * |
| Venous (PRES.) mm Hg | 45 | 110 | 180 | 270 | 310 | * |

TABLE 2

TRIPLE LUMEN CATHETER FLOW DATA FOR FIG. 9 DESIGN

| Flow Rate mL/Min. | 50 | 100 | 150 | 200 | 250 | 300 |
|---|---|---|---|---|---|---|
| Arterial (VAC) mm Hg | 70 | 130 | 160 | * | * | * |
| Venous (PRES.) mm Hg | 40 | 95 | 150 | 210 | * | * |

As known by those skilled in the art, a screw extruder may be used to manufacture bulk extruded silicone tubing and strapping, and such a device together with a hot air vulcanizer are preferably used to manufacture the catheter 110 of the invention. The procedures for operating a conventional screw extruder, such as a Model #72587 Large Screw Extruder, and completing the manufacture of a catheter 110 in accordance with the invention will now be described.

First, the milled or softened silicone is stripped into sheets that are 3/8 to 5/8 inch thick and is laid onto clean polyethylene sheeting. Techniques for milling and softening silicone rubber elastomers are believed to be known to those skilled in the art and will not be discussed in further detail herein. The sheet of silicone is then cut into strips approximately 1/2 to 2 inches wide. The extruder is then started. The rheostat of the preheating unit of the extruder is then set by increasing the setting until the surface markings of the tube 112 caused by the belt in the hot air vulcanizer are removed. Alternatively, the rheostat may be set to a value appropriate to the material being run on the extruder by referencing previous manufacturing runs. The face plate located at the exit end of the extruder screw barrel is then removed. The mesh screen on the inside of the face plate is also removed and replaced with a clean #60 mesh screen.

If the same tubing construction from a previous run is being repeated, the reference die and mandrel from the previous manufacturing run is selected. Alternatively, the manufacturing information on the log sheets for the tubing which fits the general parameters of dimensions and density are referenced. Similar die/mandrel combinations for new structures are used. A mandrel with the cross-section illustrated in FIG. 11 is then inserted onto the open end of the mandrel holder on the face plate with the flat end of the mandrel facing the set screws. The mandrel is secured by tightening the set screws. The die is placed onto the die holder and secured into place with cap screws. The extruder head is then screwed into position on the threaded sections of the face plate. Next, the screw extruder is started at low speeds with the die head facing upward. If the silicone flow is not "on-center" (i.e., the silicone will form a column of silicone 1 to 1½ inches straight up from the die head), the cap screws are adjusted until the flow from the die head is straightened. Once the silicone flow is centered, the die head is re-positioned to feed material into the preheater of the hot air vulcanizer.

A high temperature thermometer is then preheated to 200° F. and placed on the conveyor belt of the hot air vulcanizer. The thermometer is sent through the hot air vulcanizer, and the temperature setting is adjusted until the thermometer reads 385° F.±5° F. The extruder is positioned so that the tubing passes through the middle of the static eliminator preheating station elements and onto the Hot Air Vulcanizer belt. Twenty-five to thirty feet of tubing are then extruded and allowed to go through the Hot Air Vulcanizer. The tubing is then inspected visually for air bubbles, discoloration, unacceptable extrusion markings, and the like.

The tubing so manufactured is then measured and cut using a guillotine cutter, and the cross-section of the tubing is inspected. If the tubing is within tolerance, the extruder is ready for a production run. Otherwise, the extruder settings are adjusted as appropriate. If the silicone used during the production run is a peroxide cured rubber, the tubing is wound around curing drums, and the curing drums are placed into an oven and cured at 400° F. for four hours. All cured tubing is then in- process tested for stretch cracking by stretching it and checking for damage.

Once the tubing is formed, the hub 122 is formed about the proximal end of the tubing as described above. Extension tubes 124, 126, and 128, clamps 130, 132, and 134, and luer connectors 142, 144, and 146 are then added as described above. The polyester cuff 120 is then placed around the tubing 112. Finally, if the catheter 110 is to have a tip, the tip is formed in a conventional manner. On the other hand, if the catheter has a blunt tip as described above, then at some time prior to use a portion of the distal end of the arterial lumen 118 is cut away to expose the arterial lumen at a point upstream of the venous lumen 116 to prevent mixing of the treated and untreated blood. The catheter 110 is then ready for insertion into the patient.

As noted above, the lumens of the catheter 110 of the invention have been designed to have equal or better flows to the known triple lumen critical care catheters without sacrificing the structural integrity of the catheter. It has been discovered that equal or greater flow characteristics could be obtained without the outer walls of the catheter collapsing during use by making the catheter lumens smooth in profile (i.e., circular or ellipsoidal) and by providing unbalanced lumen areas. In particular, it has been found that by allowing the arterial lumen to have a 10–30% size advantage over the venous lumen that lower pressures and vacuums could be achieved at higher flow rates, as depicted in Tables 1 and 2.

Those skilled in the art will appreciate that there is a limit to the size of the lumens within a given outer diameter of the catheter because the outer walls will become too thin to extrude and the lumens will be prone to collapse. During extrusion, the wall thickness and consistency is the most difficult variable to control. As the walls become too thick, a lack of lumen area exists, while as the walls become too thin, the rubber has more difficulty filling the wall area, which leads to unfilled portions of the wall. On the other hand, the wall may be thin in one area and thick in another. In fact, for the 13 french size tested to provide the data in Table 2, it was not possible with the given machinery to extrude the tubing of the "longhorn" catheter with lumens any larger than approximately 0.00327 square inch in cross-section because as the lumen sizes were increased the outer walls of the catheter became too thin to extrude. By contrast, the geometry of the design of FIGS. 11 and 12 permitted extrusion of tubing with greater internal lumen cross-sectional areas without compromising the wall structure. As reflected in Tables 1 and 2, the larger cross-sectional areas and smoother contours of the lumens of the design of the invention permitted greater flow rates to be achieved for a given outer diameter.

Thus, the catheter of the invention provides suitable flow rates for hemodialysis and other critical care uses by providing unique geometries and size relationships between the venous and arterial lumens. Such designs are counter to the conventional wisdom which suggests that maximum flow rates are achieved by strictly maximizing the cross-sectional area of each lumen within the catheter with less regard for geometry. The catheter 110 of the invention is thus believed to provide a substantial unanticipated improvement in flow rates for triple lumen catheters of a particular french size.

It will be appreciated by those skilled in the art that the foregoing has set forth the presently preferred embodiments of the invention but that numerous alternative embodiments are possible without departing from the novel teachings and advantages of the invention. For example, the venous lumen 116 may also have an ellipsoidal cross-section so long as the size relationship with the arterial lumen 118 is maintained. Accordingly, all such modifications are intended to be included within the scope of the appended claims.

I claim:

1. A multi-lumen catheter for removing a patient's untreated blood and its constituents for treatment by an extracorporeal blood treatment device and simultaneously returning treated blood and its constituents from said extracorporeal blood treatment device to the patient, said catheter comprising an elongated cylindrical tube with at least first, second and third lumens formed therein, said first lumen adapted to accept at least one of a guide wire for guiding said catheter during insertion into a blood vessel of the patient and therapeutics for introduction into the patient's bloodstream, said second lumen being adapted to return said treated blood and its constituents from said extracorporeal blood treatment device to said patient's blood vessel and having a substantially smooth, circular cross-section that provides smooth flow, and said third lumen being adapted to extract untreated blood and its constituents from said patient's blood vessel for treatment by said extracorporeal blood treatment device and having a substantially smooth, ellipsoidal cross-section that provides smooth flow and a cross-sectional area which is at least 10 percent larger than a cross-sectional area of said second lumen, whereby hydrostatic pressures in said second and third lumens are maintained within a maximum acceptable hydrostatic pressure limit for a patient during treatment of said patient's blood and its constituents at a given flow rate, and whereby flow rates in said second and third lumens are balanced at said given flow rate during treatment of said patient's blood so as to enable said extracorporeal blood treatment device to return said treated blood and its constituents to the patient's blood vessel via said second lumen at said given flow rate and simultaneously extract said untreated blood and its constituents from said blood vessel via said third lumen at said given flow rate.

2. A catheter as in claim 1, wherein said third lumen has tapered ends at respective ends along a major axis of said ellipsoidal cross-section of said third lumen so as to form a substantially football-shaped cross-section.

3. A catheter as in claim 1, wherein said third lumen has a substantially elliptical cross-section.

4. A catheter as in claim 1, wherein said third lumen has a cross-sectional area which is approximately 10–30 percent larger than a cross-sectional area of said second lumen.

5. A catheter as in claim 4, wherein said third lumen has a cross-sectional area which is approximately 25 percent larger than a cross-sectional area of said second lumen.

6. A catheter as in claim 1, wherein said catheter is sized to fit through a 13 french spreadable sheath, and said second and third lumens are sized such that when said given flow rate in said second and third lumens is approximately 250 mL/min., said hydrostatic pressure in said second lumen is approximately 310 mm Hg. and said hydrostatic pressure in said third lumen is approximately 160 mm Hg.

7. A system for extracorporeal treatment of a patient's blood and its constituents, comprising:

an extracorporeal blood treatment device;

a multi-lumen catheter for removing the patient's untreated blood and its constituents for treatment by said extracorporeal blood treatment device and simultaneously returning treated blood and its constituents from said extracorporeal blood treatment device to the patient, said catheter comprising an elongated cylindrical tube with at least first, second and third lumens formed therein, said first lumen adapted to accept at least one of a guide wire for guiding said catheter during insertion into a blood vessel of the patient and therapeutics for introduction into the patient's bloodstream, said second lumen being adapted to return said treated blood and its constituents from said extracorporeal blood treatment device to said patient's blood vessel and having a substantially smooth, circular cross-section that provides smooth flow, and said third lumen being adapted to extract untreated blood and its constituents from said patient's blood vessel for treatment by said extracorporeal blood treatment device and having a substantially smooth, ellipsoidal cross-section that provides smooth flow and a cross-sectional area which is at least 10 percent larger than a cross-sectional area of said second lumen, whereby hydrostatic pressures in said second and third lumens are maintained within a maximum acceptable hydrostatic pressure limit for a patient during treatment of said patient's blood and its constituents at a given flow rate, and whereby flow rates in said second and third lumens are balanced at said given flow rate during treatment of said patient's blood so as to enable said extracorporeal blood treatment device to return said treated blood and its constituents to the patient's blood vessel via said second lumen at said given flow rate and simultaneously extract said untreated blood and its constituents from said blood vessel via said third lumen at said given flow rate; and a hub containing at least first and second extension tubes respectively connected to distal ends of said second and third lumens, said first extension tube providing a passageway from the distal end of said second lumen through said hub to an output of said extracorporeal blood treatment device, and said second extension tube providing a passageway from the distal end of said third lumen through said hub to an input of said extracorporeal blood treatment device so as to form a closed system in which untreated blood is extracted from said patient for treatment by said extracorporeal blood treatment device and treated blood is returned to said patient.

8. A system as in claim 7, wherein said third lumen of said catheter has tapered ends at respective ends along a major axis of said ellipsoidal cross-section of said third lumen so as to form a substantially football-shaped cross-section.

9. A system as in claim 7, wherein said third lumen of said catheter has a substantially elliptical cross-section.

10. A system as in claim 7, wherein said third lumen of said catheter has a cross-sectional area which is approximately 10–30 percent larger than a cross-sectional area of said second lumen.

11. A system as in claim 10, wherein said third lumen of said catheter has a cross-sectional area which is approximately 25 percent larger than a cross-sectional area of said second lumen.

12. A system as in claim 7, wherein said catheter is sized to fit through a 13 french spreadable sheath, and said second and third lumens are sized such that when said given flow rate in said second and third lumens is approximately 250 mL/min., said hydrostatic pressure in said second lumen is approximately 310 mm Hg. and said hydrostatic pressure in said third lumen is approximately 160 mm Hg.

13. A method of treating a patient's blood and its constituents using an extracorporeal blood treatment device, comprising the steps of:

inserting a multi-lumen catheter into a blood vessel of the patient, said catheter comprising an elongated cylindrical tube with at least first, second and third lumens formed therein, said first lumen adapted to accept at least one of a guide wire for guiding said catheter during insertion into the blood vessel of the patient and therapeutics for introduction into the patient's bloodstream, said second lumen being adapted to return treated blood and its constituents from said extracorporeal blood treatment device to the patient's blood vessel and having a substantially smooth, circular cross-section that provides smooth flow, and said third lumen being adapted to extract untreated blood and its constituents from the patient's blood vessel for treatment by said extracorporeal blood treatment device and having a substantially smooth, ellipsoidal cross-section that provides smooth flow and a cross-sectional area which is at least 10 percent larger than a cross-sectional area of said second lumen, said catheter further comprising a hub containing at least first and second extension tubes respectively connected to distal ends of said second and third lumens;

connecting said first extension tube to an output of said extracorporeal blood treatment device so as to provide a passageway from the distal end of said second lumen through said hub to said output of said extracorporeal blood treatment device;

connecting said second extension tube to an input of said extracorporeal blood treatment device so as to provide a passageway from the distal end of said third lumen through said hub to said input of said extracorporeal blood treatment device; and said extracorporeal blood treatment device simultaneously extracting untreated blood and its constituents from said patient through said third lumen for treatment and returning treated blood and its constituents to said patient through said second lumen at substantially equal flow rates so as to balance flows in said second and third lumens and so as to maintain hydrostatic pressures in said second and third lumens within a maximum acceptable hydrostatic pressure limit for the patient during treatment of the patient's blood and its constituents.

* * * * *

UNITED STATES PATENT AND TRADEMARK OFFICE
CERTIFICATE OF CORRECTION

PATENT NO. : 6,146,354
DATED : November 14, 2000
INVENTOR(S) : Beil

It is certified that error appears in the above-identified patent and that said Letters Patent is hereby corrected as shown below:

Cover Page, Line 3 of "ABSTRACT" delete "inside." and insert --therein.-- therefor.
Column 3, Line 46 insert --apheresis-- between "care" and "catheter".
Column 5, Line 17, delete "silicon" and insert --silicone-- therefor.

Signed and Sealed this

Eighth Day of May, 2001

Attest:

NICHOLAS P. GODICI

Attesting Officer

Acting Director of the United States Patent and Trademark Office